United States Patent [19]

Elm et al.

[11] Patent Number: 4,552,753
[45] Date of Patent: Nov. 12, 1985

[54] PROCESS FOR MAKING ROLL-ON ANTIPERSPIRANT COMPOSITIONS

[75] Inventors: Chance R. Elm, Cincinnati; Erlend R. Lowrey, Greenhills, both of Ohio

[73] Assignee: The Procter & Gamble Company, Cincinnati, Ohio

[21] Appl. No.: 556,883

[22] Filed: Dec. 1, 1983

[51] Int. Cl.$^4$ .......................... A61K 7/32; A61K 7/34; A61K 7/38
[52] U.S. Cl. ......................................... 424/66; 424/68
[58] Field of Search .............................. 424/66, 68, 65

[56] References Cited

U.S. PATENT DOCUMENTS

| 4,053,581 | 10/1977 | Pader et al. | 424/47 |
| 4,062,986 | 12/1977 | Billerbeck et al. | 426/633 |
| 4,065,564 | 12/1977 | Miles, Jr. et al. | 424/66 |
| 4,073,880 | 2/1978 | Pader et al. | 424/68 |
| 4,073,880 | 2/1978 | Pader et al. | 424/68 |
| 4,278,655 | 7/1981 | Elmi | 424/68 |
| 4,368,184 | 1/1983 | Drucker et al. | 424/66 |

FOREIGN PATENT DOCUMENTS 2018590 10/1979 United Kingdom ................. 424/68
2072503 10/1981 United Kingdom ................. 424/68

OTHER PUBLICATIONS

Cosmetics & Toiletries, 4/1980, vol. 95, pp. 102 and 103.
Lachman et al., The Theory & Practice of Industrial Pharmacy, 2nd ed., 1976, pp. 612 to 614.

Primary Examiner—Dale R. Ore
Attorney, Agent, or Firm—David L. Suter; Douglas C. Mohl; Richard C. Witte

[57] ABSTRACT

Processes, for making roll-on antiperspirant compositions, comprising the steps of preparing a composition comprising one or more volatile silicone oils, one or more non-volatile silicone oils and an antiperspirant active; deaerating the composition; and filling a roll-on container with the composition. Preferably, the composition is milled either before or after deaeration. Especially preferred are compositions comprising from about 10% to about 90% of one or more volatile silicone oils, from about 1% to about 35% of one or more non-volatile silicone oils, from about 10% to about 70% of an antiperspirant active, and from about 1% to about 15% of a bulking/suspending material.

12 Claims, No Drawings

PROCESS FOR MAKING ROLL-ON ANTIPERSPIRANT COMPOSITIONS

BACKGROUND OF THE INVENTION

The present invention relates to processes for making roll-on antiperspirant compositions. More particularly, it relates to compositions, and processes for making such compositions, with improved compositional stability.

Compositions designed to stop or reduce the flow of human perspiration are well-known in the chemical and cosmetic literature. Such antiperspirant compositions may be applied to the skin by a variety of methods. For example, S. Plechner, "Antiperspirants and Deodorants," 2 *Cosmetics, Science and Technology*, 373–416 (M. Balsam and E. Sagarin ed. 1972), describes antiperspirant compositions in spray, roll-on, cream, and stick forms. For a variety of reasons, one preferred method of application is as a roll-on.

Roll-on antiperspirants, however, may present certain disadvantages, particularly with respect to cosmetic characteristics. The literature describes many formulations which attempt to provide cosmetically-acceptable roll-on products. A particularly preferred group of roll-on products incorporate volatile silicones. Such compositions are described in U.S. Pat. No. 4,053,581, Pader et al., issued Oct. 11, 1977; U.S. Pat. No. 4,065,564, Miles, Jr., et al., issued Dec. 27, 1977; U.S. Pat. No. 4,073,880, Pader, et al., issued Feb. 14, 1978; and British Patent Application No. 2,018,590, Elmi, et al., published Oct. 24, 1979.

It has been discovered that such compositions that contain mixtures of volatile and non-volatile silicones are subject to compositional instability. In particular, a phenomenon, herein referred to as "creep", takes place wherein the silicone oils in the antiperspirant compositions migrate up the walls of the product container and eventually deposit on the exterior of the container. This problem leads to loss of product materials, poor package aesthetics, and other undesired effects.

It has now been discovered that antiperspirant roll-on compositions, containing volatile and non-volatile silicone oils, have improved compositional stability when such compositions are made by a process in which the product is deaerated prior to filling into a roll-on container. In particular, silicone-containing antiperspirant roll-on compositions, made by the processes of this invention, exhibit reduced incidence of the "creep" phenomenon.

SUMMARY OF THE INVENTION

The present invention provides a process, for making an antiperspirant composition that is to be applied by means of a roll-on container, comprising the steps of preparing a composition comprising one or more volatile silicone oils, one or more non-volatile silicone oils and an antiperspirant active; deaerating said composition; and filling said roll-on container with said composition. Preferably, the compositions of the present invention comprise:

(a) from about 10% to about 90% of one or more volatile silicone oils;
(b) from about 1% to about 35% of one or more non-volatile silicone oils;
(c) from about 10% to about 70% of an antiperspirant active.

Preferably, the instant processes also include a milling step either before or after the deaeration step. Also preferably, the deaeration step in the process of the instant invention is performed at an absolute pressure of no greater than about 300 millibars.

DESCRIPTION OF THE INVENTION

The antiperspirant compositions of the present invention contain three essential ingredients: one or more volatile silicone oils, one or more non-volatile silicone oils, and an antiperspirant "active" material. These compositions encompass any liquid composition intended for human use in order to deposit antiperspirant materials on human tissue. Specifically, such compositions are to be applied using roll-on containers.

Preferably the compositions of the present invention comprise:

(a) from about 10% to about 90% of one or more volatile silicone oils;
(b) from about 1% to about 35% of one or more non-volatile silicone oils;
(c) from about 10% to about 70% of an antiperspirant active.

(All percentages herein are by weight of total composition.) More preferably, the instant compositions comprise from about 15% to about 70% of the volatile silicone oils. Also more preferably, the compositions contain from about 5% to about 30% of the non-volatile silicone oils.

Components

Volatile Silicone Oils:

The compositions of the instant invention incorporate one or more volatile silicone oils. As used herein, "volatile" refers to those oils which have a measurable vapor pressure at ambient conditions. The volatile silicone oils of this invention may be cyclic or linear. A description of various volatile silicone oils is found in Todd, et al., "Volatile Silicone Fluids For Cosmetics" *Cosmetics and Toiletries*, 91, 27–32 (1976), incorporated by reference herein. Preferred silicone oils include those containing from about 3 to about 9 silicon atoms, preferably containing from about 4 to about 5 silicon atoms. Cyclic volatile silicones useful in the instant compositions include those of the following formula:

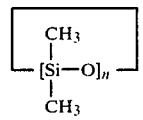

wherein n=3 to 7. Linear volatile silicone oils include those of the following formula:

wherein n=1 to 7. Linear volatile silicones generally have viscosities of less than about 5 centistokes at 25° C., while the cyclic materials have viscosities of less than about 10 centistokes. Examples of silicone oils useful in the present invention include: Dow Corning 344, Dow Corning 345, and Dow Corning 200 (manufactured by the Dow Corning Corporation); 7207 and 7158 (manufactured by the Union Carbide Corporation); SF 1202 (manufactured by General Electric); and SWS-03314 (manufactured by SWS Silicones Corporation). Roll-on formulations incorporating volatile silicone oils, in proportions useful in the present invention, are disclosed in the following patent documents, incorporated by reference herein: U.S. Pat. No. 4,053,581, Pader, et al., issued Oct. 11, 1977; U.S. Pat. No. 4,073,880, Pader, et al., issued Feb. 14, 1978; British Patent Application No. 2,018,590, Elmi, et al., published Oct. 24, 1979; and U.S. Patent Application Ser. No. 163,903, Beckmeyer, et al., filed June 30, 1980, now abandoned.

Non-Volatile Silicone Oils:

The compositions of this invention also contain one or more non-volatile silicone oils. These non-volatile silicone fluids may be either a polyalkylsiloxane, a polyalkylarylsiloxane, or a polyethersiloxane copolymer. The essentially non-volatile polyalkylsiloxanes that may be used include, for example, polydimethylsiloxanes with viscosities ranging from about 5 to about 100,000 centistokes at 25° C. These siloxanes are commercially available as, e.g., Vicasil (sold by the General Electric Company) and the Dow Corning 200 series (sold by the Dow Corning Corporation).

The essentially non-volatile polyalkylarylsiloxanes that may be used include, for example, polymethylphenylsiloxanes having viscosities of 15 to about 1000 centistokes at 25° C. Examples of commercially available siloxanes include SF 1075 methylphenyl fluid (sold by the General Electric Company) and 556 cosmetic grade fluid (sold by the Dow Corning Corporation).

The essentially non-volatile polyethersiloxane copolymers that are useful herein include a dimethylpolyoxyalkylene ether copolymer fluid having a nominal viscosity of from about 1200 to about 1500 centistokes at 25° C. This copolymer is available, for example, from the General Electric Company as SF-1066 organo silicone surfactant. Preferred compounds of this type are polysiloxane ethylene glycol ether copolymers.

Roll-on compositions incorporating non-volatile silicone oils, in proportions useful herein, are disclosed in the following patent dcuments, incorporated by reference herein: U.S. Pat. No. 4,053,581, Pader, et al., issued Oct. 11, 1977; U.S. Pat. No. 4,065,564, Miles, Jr., et al., issued Dec. 27, 1977; and U.S. Patent Application Ser. No. 163,903, Beckmeyer, et al., filed June 30, 1980, now abandoned.

Antiperspirant Actives:

The instant antiperspirant compositions contain a safe and effective amount of one or more components, herein "antiperspirant actives", which are meant to be deposited upon human tissue. A "safe and effective" amount of an antiperspirant active is that amount which yields the desired astringent benefit at a reasonable benefit/risk ratio for human usage. Astringent metallic salts are preferred antiperspirant actives, and may be incorporated in the instant compositions at levels of from about 10% to about 70%, preferably from about 15% to about 50%, most preferably from about 15% to about 40%.

Preferred astringent metallic salts include the inorganic and organic salts of aluminum, zirconium and zinc, and mixtures thereof. Particularly preferred are the aluminum and zirconium salts, such as aluminum halides, aluminum hydroxy halides, zirconyl oxyhalides, zirconyl hydroxy halides, and mixtures thereof. Preferred aluminum salts include those of the formula:

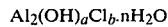

$Al_2(OH)_aCl_b \cdot nH_2O$ wherein a is from about 2 to about 5; $a+b=6$; n is from about 1 to about 6; and wherein a, b, and n may have non-integer values. A particularly preferred aluminum salt of the above formula is 5/6 basic aluminum chlorhydrate, wherein $a=5$.

Processes for preparing aluminum salts are disclosed in the following documents, all incorporated by reference herein: U.S. Pat. No. 3,887,692, Gilman, issued June 3, 1975; U.S. Pat. No. 3,904,731, Jones et al., issued Sept. 9, 1975; U.S. Pat. No. 4,359,456, Gosling, et al., issued Nov. 16, 1982; and British Patent Specification No. 2,048,229, Fitzgerald, et al., published Dec. 10, 1980. Preferred mixtures of aluminum salts, in roll-on compositions useful herein, are disclosed in U.S. Patent Application Ser. No. 546,806, Thurston, et al., filed Oct. 31, 1983, (incorporated by reference herein), now abandoned.

Zirconium salts are also preferred for use in the compositions of the present invention. Preferred zirconyl hydroxychloride salts are of the general formula:

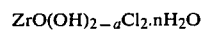

$ZrO(OH)_{2-a}Cl_2 \cdot nH_2O$ wherein a is from about 1.5 to about 1.87; x is from about 1 to about 7; and wherein a and n may have non-integer values. These zirconium salts are disclosed in Belgian Pat. No. 825,146, issued Aug. 4, 1975 (incorporated by reference herein). Particularly preferred zirconium salts are those complexes that also contain aluminum and glycine, commonly known as "ZAG" complexes. Such ZAG complexes contain aluminum chlorhydrate and zirconyl hydroxychloride of the formulae detailed above. These compounds in ZAG complexes are disclosed in U.S. Pat. No. 3,679,068, Luedders, et al., issued Jan. 12, 1974 (incorporated herein by reference), and U.S. Pat. No. 4,120,938, Shelton, issued Oct. 17, 1978 (incorporated by reference herein).

Non-essential Components:

The compositions of this invention preferably contain optional components which modify the physical characteristics of the roll-on products. Such components include emollients, bulking/suspending aids, colorants, perfumes, and emulsifiers. In particular, the instant antiperspirant; compositions also preferably contain an emollient. While the non-volatile silicone oils described herein are preferred emollients, other emollients suitable for use in the present invention include fatty acid and fatty alcohol esters and water insoluble ethers, such as those disclosed in U.S. Pat. No. 4,202,879, Shelton, issued May 13, 1980 (incorporated by reference herein). Emollients generally useful herein are described in U.S. patent application Ser. No. 163,903, Beckmeyer, et al., filed June 30, 1980, (incorporated by reference herein), now abandoned. The total level of emollient incorporated in the instant compositions (including the non-volatile silicone oils) is from about 1% to about 35%.

Bulking agents/suspending agents and/or inert filler materials are also useful in the instant compositions. Such materials include talc, colloidal silcates, clays, and mixtures thereof, at levels of from about 1% to about 15% of the composition. Clay bulking/suspending agents useful herein include those selected from the group consisting of montmorillonite clays and hydrophobically treated montmorillonites, e.g., bentonites, hectorites, and colloidal magnesium aluminum silicates. The use of bulking agents in roll-on compositions is disclosed in U.S. patent application Ser. No. 163,903.

Beckmeyer, et al., filed June 30, 1980, (incorporated by reference herein), now abondoned.

The compositions of the present invention may also contain such other components as perfumes, coloring agents, emulsifiers, and deodorant materials such as bacteriocides and fungicides. If present, these components comprise from about 0.002% to about 10% of the composition.

Processes

The processes of the instant invention comprise the steps of:
(1) preparing a composition comprising one or more volatile silicone oils, one or more non-volatile silicone oils, and an antiperspirant active;
(2) deaerating said composition; and
(3) filling a roll-on container with said composition.

The individual steps in the instant processes involve methods well-known in the art. The particular methods that are used may vary depending upon such factors as the volume of product that is to be produced, the types of equipment to be used, and the particular composition of the product. In a commercial application, for example, the steps of the present processes may be performed sequentially in a continuous process, or as the individual steps in a batch process. As used herein, the term "bulk" composition shall refer to the compositions of this invention generally, at least comprising the volatile and non-volatile silicone oils, without regard to the volume of product or the particular methods employed.

The step of preparing the bulk composition generally consists of simple admixture of the volatile silicone oils, non-volatile silicone oils, and the antiperspirant active. Such admixture is generally performed at ambient conditions. Preferably, any optional components are also admixed into the bulk composition along with the essential components, although process variations could allow admixture of optional components at any point prior to the filling step of the present processes.

The processes of the instant invention incorporate a deaeration step, whereby the compositions of the present invention are passed through a deaerator. As used herein, the term "deaeration" refers to any process of dispersion under vacuum, regardless of the extent to which air or gasses are removed or the particular mechanism by which the instant processes effect reduction of creep. Several commercially-available deaeration devices may be used, including those made by Fryma, Inc. and the Cornell Machine Company. Operation of such deaerators generally consists of introducing a bulk solution into a deaeration vessel, dispersing the solution under vacuum, collecting the solution, and then removing the solution from the deaeration vessel. Each of these steps may be performed through a variety of means. For example, dispersion may be effected through pumping a bulk solution into a spinning apparatus and, by centrifugal force, driving the solution through a screen, under vacuum. In the instant processes, the deaeration step is preferably performed under vacuum, at an absolute pressure no greater than about 300 millibars, more preferably at an absolute pressure no greater than about 200 millibars, most preferably at an absolute pressure no greater than about 60 millibars. As referenced herein, all pressures are absolute, in millibar units (1 mbar=1000 dyne-cm$^{-2}$).

A preferred process of the instant invention incorporates a deaeration step wherein a bulk solution is introduced into a Fryma Model VE-1 Deaerator, at a flow rate of approximately 41 kilograms per minute, maintained at a pressure of 60 millibars. It should be understood that the deaeration steps described above are those which may be utilized in a commercial application, and do not describe all of the deaeration methods which may be used in the instant processes.

The filling step in the processes of the present invention also utilizes methods well-known in the art. The step may be performed immediately after the mixing and deaeration, or the bulk solution may be stored prior to filling. Roll-on containers useful herein are, for example, commercially available from a variety of sources. Such containers are described in the following patent documents, incorporated by reference herein: U.S. Pat. No. 2,823,403, Whitney, issued Feb. 18, 1958; U.S. Pat. No. 3,075,230, Marchant, issued Jan. 29, 1963; and U.S. Pat. No. 3,361,305, Spatz, issued Jan. 2, 1968. Preferred containers, useful herein, are described in U.S. Pat. No. 4,221,495, Braun, et al., issued Sept. 9, 1980 (incorporated by reference herein).

The processes of the present invention perferably also include an additional step whereby the bulk compositions are milled either before or after deaeration. Thus, the milling and deaerating steps of such preferred processes may be performed in either order, i.e. the bulk composition may be milled and then deaerated, or deaerated and then milled. Incorporation of a milling step in the instant processes is particularly preferred when the compositions of the present invention contain optional bulking/suspending materials.

Milling generally consists of any high shear mixing process. By varying the pressure at which the milling is effected, the viscosity of the bulk solution may be changed. One of several commercially-available homogenizing mills may be used, such as those sold by Gaulin Corp., Cornell Machine Company, Sonic Industries, Inc., and Cherry-Burrell (AMCA International Corp.). A preferred milling process step is performed using a Gaulin M-3 Homogenizer.

The following non-limiting examples illustrate the compositions, processes and uses of the present invention.

EXAMPLE I

A roll-on antiperspirant composition, encompassed by the present invention, was produced with the following components:

| Components | Weight % |
| --- | --- |
| cyclomethicone (D4/D5) | 53.8 |
| dimethicone (100 cs) | 9.08 |
| dimethicone (350 cs) | 0.92 |
| ZAG complex* | 26.7 |
| Microthene ®** | 7.0 |
| Bentone 38 ®*** | 1.0 |
| Cab-O-Sil**** | 0.7 |
| propylene carbonate | 0.3 |
| fragrance | 0.5 |

*Zirconium-aluminum-glycine-hydroxychloride complex antiperspirant active, sold by Reheis Chemical Company.
**Low density polyethylene powder, sold by U.S.I. Chemicals.
***Hydrophobic bentonite suspending agent, sold by NL Industries, Inc..
****Colloidal silicate sold by Cabot Corp.

The components recited above were mixed into a bulk composition, at ambient conditions. At a flow rate of approximately 41 kilograms per minute, the composition was introduced into a Gaulin M3 Homogenizer, at a pressure of approximately 1.38×10$^5$ millibars. The bulk composition was then pumped, at a flow rate of approximately 41 kilograms per minute, into a Fryma VE-1 Deaerator, maintained at a pressure of approximately 60 millibars, and then pumped into a storage container. Thereafter, the product was filled into a roll-on container similar to those disclosed in U.S. Pat. No. 4,221,495, Braun, et al., issued Sept. 9, 1980. The container was then capped, applying torque equivalent to approximately 20 to 27 N-m release torque, determined 5 minutes after the product is capped. The product, when applied to the skin of a human subject, is effective as an antiperspirant. In the example above, the process described may be varied by reversing the milling and deaerating steps, with substantially similar results.

EXAMPLE II

A roll-on composition, encompassed by the present invention, is made comprising:

| Components | Weight % |
| --- | --- |
| 5/6 basic aluminum chlorhydrate (dihydrate)* | 26.70 |
| aluminum chloride (hexahydrate)* | 6.50 |
| cyclomethicone (D5) | 46.78 |
| dimethicone (350 cs) | 5.00 |
| dimethicone (100 cs) | 5.00 |
| Cab-O-Sil | 2.00 |
| Microthene ® | 7.00 |
| sulfated castor oil | 1.00 |
| ethylene brassylate | 0.02 |

*Components of a dual powder mixture, as described in U.S. Pat. Application Ser. No. 546,806, Thurston, et al., filed October 31, 1983, now abandoned.

An antiperspirant composition, as comprised above, is made by the method described in Example I. The product, when applied to the skin of a human subject, is effective as an antiperspirant.

EXPERIMENT I

Two groups of roll-on antiperspirant products, with 200 bottles per group, were made according to the composition and process described in Example I. Two additional groups, of 200 bottles each, were made according to the process of Example I, but without the deaeration step. Thereafter, one deaerated group and one non-deaerated group were stored at about 27° C., and one deaerated group and one non-deaerated group were stored at about 38° C. At periods of one, two, and three months after manufacture, the bottles in all four groups were observed for deposition of any silicone material (caused by creep) on the outside of the bottles. Table I, below, presents the results of these observations for each of the four groups, shown as the percent of bottles in each group which showed creep.

TABLE I

| Time Elapsed | Group | Deaerated | % with Creep |
| --- | --- | --- | --- |
| Creep at 27° C. | | | |
| 1 month | 1 | No | 0.5 |
| 1 month | 2 | Yes | 0 |
| 2 months | 1 | No | 2.5 |
| 2 months | 2 | Yes | 0.5 |
| 3 months | 1 | No | 5.0 |
| 3 months | 2 | Yes | 2.0 |
| Creep at 38° C. | | | |
| 1 month | 3 | No | 13.0 |
| 1 month | 4 | Yes | 0 |
| 2 months | 3 | No | 20.5 |
| 2 months | 4 | Yes | 1.0 |
| 3 months | 3 | No | 30.0 |

TABLE I-continued

| Time Elapsed | Group | Deaerated | % with Creep |
| --- | --- | --- | --- |
| 3 months | 4 | Yes | 1.5 |

The data presented in Table I demonstrates that roll-on antiperspirant products made by the processes of the instant invention exhibit reduced creep phenomena.

EXPERIMENT II

Seven batches of an unscented antiperspirant composition were produced in a manner similar to that described in Example I. (Compositions were as in Example I, substituting 0.02% ethylene brassylate for the fragrance and increasing the overall level of the silicone materials by 0.48%.) However each batch was subjected to a different vacuum level during the deaeration step. Each batch was then filled into a group of 300 bottles, for a total of seven groups of 300 bottles each.

The bottles in each group were then stored for a period of one month at about 38° C., with the exception of those in Group 4, which were stored for two weeks at about 38° C. Thereafter the bottles in each group were observed for evidence of any silicone oils on the outside of the package (caused by creep). Table II, below, presents observations for each of the seven groups, shown as a percent of bottles with observed creep as a function of the pressure (vacuum level) used in deaerating the bottled compositions in that group.

TABLE II

| Group | Deaeration Pressure | % with creep |
| --- | --- | --- |
| 1 | ambient* | 33.3 |
| 2 | 510 | 24.7 |
| 3 | 460 | 35.7 |
| 4 | 360 | 25.3 |
| 5 | 260 | 6.7 |
| 6 | 160 | 0 |
| 7 | 60 | 0 |

*approximately 1000 mbar

This data demonstrates that the processes of the instant invention, when performed at preferred vacuum levels in the deaeration step, yield improved antiperspirant products.

What is claimed is:

1. In an improved process for making a stable roll-on antiperspirant composition comprising the steps of preparing a composition comprising one or more volatile silicone oils, one or more non-volatile silicone oils, and an antiperspirant active, and filling a roll-on container with said composition, wherein the improvement comprises the step of deaerating said composition prior to said filling step to exhibit reduced incidence of the creep phenomenon.

2. In a improved process, according to claim 1, wherein said composition comprises:
   (a) from about 10% to about 90% of one or more of said volatile silicone oils;
   (b) from about 1% to about 35% of one or more of said non-volatile silicone oils, and
   (c) from about 10% to about 70% of said antiperspirant active.

3. In an improved process, according to claim 1, additionally comprising the step of milling said composition either before or after said deaerating step.

4. In an improved process, according to claim 1, wherein said deaerating step is performed at a pressure no greater than about 300 millibars.

5. In an improved process, according to claim 4, wherein said deaerating step is performed at a pressure no greater than about 200 millibars.

6. In an improved process, according to claim 5, wherein said deaerating step is performed at a pressure no greater than about 60 millibars.

7. In an improved process, according to claim 2, wherein said composition additionally comprises from about 1% to about 15% of a bulking/suspending material.

8. In an improved process, according to claim 2, wherein said composition comprises from about 15% to about 70% of one or more of said volatile silicone oils.

9. In an improved process, according to claim 2, wherein said composition comprises from about 15% to about 50% of said antiperspirant active.

10. In an improved process, according to claim 9, wherein said antiperspirant active is a zirconium-aluminum-glycine complex.

11. In an improved process, according to claim 9, wherein said antiperspirant active is comprised of a mixture of aluminum chloride powder and basic aluminum chloride powder.

12. In an improved process for making a stable roll-on antiperspirant composition, comprising the steps of preparing a composition comprising from about 10% to about 90% of one or more volatile silicone oils, from about 1% to about 35% of one or more non-volatile silicone oils, from about 15% to about 50% of an antiperspirant active, and from about 1% to about 15% of a bulking suspension material, milling said composition and filling a roll-on container with said composition, wherein the improvement comprises the step of deaerating said composition prior to said filling step to exhibit reduced incidence of the creep phenomenon.

* * * * *